(12) United States Patent
Isele et al.

(10) Patent No.: US 8,632,793 B2
(45) Date of Patent: *Jan. 21, 2014

(54) TOP-BIASED BENEFICIAL COMPONENTS ON SUBSTRATES

(75) Inventors: Olaf Isele, West Chester, OH (US); Joseph Anthony Gatto, Loveland, OH (US); Thomas James Klofta, Cincinnati, OH (US); Matthew Gerald McNally, West Chester, OH (US); Julie Charlene Rule, Cincinnati, OH (US); James Anthony Staudigel, Cincinnati, OH (US); Kirsten Kae Stone, West Chester, OH (US); Sherman Lee Taylor, II, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 810 days.

This patent is subject to a terminal disclaimer.

(21) Appl. No.: 11/654,086

(22) Filed: Jan. 17, 2007

(65) Prior Publication Data

US 2007/0116748 A1 May 24, 2007

Related U.S. Application Data

(63) Continuation of application No. 09/895,027, filed on Jun. 29, 2001, now Pat. No. 7,166,292.

(51) Int. Cl.
*A01N 25/34* (2006.01)
*A61F 13/00* (2006.01)
*A61K 9/00* (2006.01)

(52) U.S. Cl.
USPC ........... 424/402; 424/400; 424/401; 424/443; 424/446

(58) Field of Classification Search
None
See application file for complete search history.

(56) References Cited

U.S. PATENT DOCUMENTS

| | | | |
|---|---|---|---|
| 2,804,424 A | 8/1957 | Stim et al. | |
| 2,831,854 A | 4/1958 | Tucker et al. | |
| 3,489,148 A | 1/1970 | Duncan et al. | |
| 3,490,454 A | 1/1970 | Goldfarb et al. | |
| 3,567,820 A * | 3/1971 | Sperti et al. | 514/735 |
| 3,585,998 A | 6/1971 | Hayford et al. | |
| 3,755,560 A | 8/1973 | Dickert et al. | |
| 3,860,003 A | 1/1975 | Buell | |
| 3,875,942 A | 4/1975 | Roberts et al. | |
| 3,896,807 A | 7/1975 | Buchalter | |

(Continued)

FOREIGN PATENT DOCUMENTS

| | | |
|---|---|---|
| CA | 2019557 | 12/1990 |
| DE | 4136540 A1 | 5/1992 |

(Continued)

OTHER PUBLICATIONS

U.S. Appl. No. 09/529,575, filed Mar. 11, 1999, Rourke, et al.

*Primary Examiner* — Lakshmi Channavajjala
(74) *Attorney, Agent, or Firm* — Richard L. Alexander

(57) ABSTRACT

A treated substrate with improved availability of a beneficial component for transfer to a target surface and methods for making the same are described. The substrate has a contacting surface with a beneficial component that is transferred from the contacting surface to a target surface during use of the article. The beneficial component is applied to the article in such a way as to "Top-Bias" the component on or near the contacting surface of the article.

16 Claims, 2 Drawing Sheets

(56) References Cited

U.S. PATENT DOCUMENTS

| | | |
|---|---|---|
| 3,902,493 A | 9/1975 | Baier et al. |
| 3,929,135 A | 12/1975 | Thompson |
| 3,929,678 A | 12/1975 | Laughlin et al. |
| 3,963,699 A | 6/1976 | Rizzi et al. |
| 4,005,195 A | 1/1977 | Jandacek |
| 4,005,196 A | 1/1977 | Jandacek et al. |
| 4,112,167 A | 9/1978 | Dake et al. |
| 4,253,461 A | 3/1981 | Strickland et al. |
| 4,263,363 A | 4/1981 | Buck et al. |
| 4,324,246 A | 4/1982 | Mullane et al. |
| 4,324,247 A | 4/1982 | Aziz |
| 4,342,314 A | 8/1982 | Radel et al. |
| 4,421,769 A | 12/1983 | Dixon et al. |
| 4,463,045 A | 7/1984 | Ahr et al. |
| 4,513,051 A | 4/1985 | Lavash |
| 4,517,360 A | 5/1985 | Volpenhein |
| 4,518,772 A | 5/1985 | Volpenhein |
| 4,556,146 A | 12/1985 | Swanson et al. |
| 4,556,560 A | 12/1985 | Buckingham |
| 4,569,343 A | 2/1986 | Kimura et al. |
| 4,589,876 A | 5/1986 | Van Tilburg |
| 4,597,760 A | 7/1986 | Buell |
| 4,597,761 A | 7/1986 | Buell |
| 4,609,518 A | 9/1986 | Curro et al. |
| 4,623,339 A | 11/1986 | Ciraldo et al. |
| 4,629,643 A | 12/1986 | Curro et al. |
| 4,666,765 A | 5/1987 | Caldwell et al. |
| 4,685,909 A | 8/1987 | Berg et al. |
| 4,687,478 A | 8/1987 | Van Tilburg |
| 4,704,112 A | 11/1987 | Suzuki et al. |
| 4,704,115 A | 11/1987 | Buell |
| 4,753,643 A | 6/1988 | Kassai |
| 4,790,836 A | 12/1988 | Brecher |
| 4,797,300 A | 1/1989 | Jandacek et al. |
| 4,882,204 A | 11/1989 | Tenenbaum |
| 4,900,317 A | 2/1990 | Buell |
| 4,904,524 A | 2/1990 | Yoh |
| 4,909,802 A | 3/1990 | Ahr et al. |
| 4,950,264 A | 8/1990 | Osborn, III |
| 4,959,059 A | 9/1990 | Eilender et al. |
| 4,964,860 A | 10/1990 | Gipson et al. |
| 4,976,953 A | 12/1990 | Orr et al. |
| 4,990,144 A | 2/1991 | Blott |
| 4,994,053 A | 2/1991 | Lang |
| 4,996,238 A | 2/1991 | Matravers |
| 5,006,394 A | 4/1991 | Baird |
| 5,009,653 A | 4/1991 | Osborn, III |
| 5,043,155 A | 8/1991 | Puchalski et al. |
| 5,069,897 A | 12/1991 | Orr |
| 5,264,460 A | 11/1993 | Jakobson et al. |
| 5,267,992 A | 12/1993 | Van Tilburg |
| 5,304,161 A | 4/1994 | Noel et al. |
| 5,306,514 A | 4/1994 | Letton et al. |
| 5,306,515 A | 4/1994 | Letton et al. |
| 5,306,516 A | 4/1994 | Letton et al. |
| 5,321,098 A | 6/1994 | Lal |
| 5,370,132 A | 12/1994 | Weber et al. |
| 5,389,094 A | 2/1995 | Lavash et al. |
| 5,413,568 A | 5/1995 | Roach et al. |
| 5,415,649 A | 5/1995 | Watanabe et al. |
| 5,460,623 A | 10/1995 | Emenaker et al. |
| 5,489,283 A | 2/1996 | Van Tillburg |
| 5,509,915 A | 4/1996 | Hanson et al. |
| 5,525,346 A | 6/1996 | Hartung et al. |
| 5,558,655 A | 9/1996 | Jezzi et al. |
| 5,569,231 A | 10/1996 | Emenaker et al. |
| 5,607,760 A | 3/1997 | Roe |
| 5,609,587 A | 3/1997 | Roe |
| 5,611,879 A * | 3/1997 | Morman ..................... 156/201 |
| 5,620,430 A | 4/1997 | Bamber |
| 5,635,191 A | 6/1997 | Roe et al. |
| 5,643,588 A | 7/1997 | Roe et al. |
| 5,968,025 A | 10/1999 | Roe et al. |
| 5,980,919 A | 11/1999 | Greenfield et al. |
| 6,060,149 A | 5/2000 | Nissing et al. |
| 6,153,209 A | 11/2000 | Vega et al. |
| 6,198,018 B1 | 3/2001 | Curro |
| 6,291,050 B1 * | 9/2001 | Cree et al. ..................... 428/131 |
| 6,426,444 B2 | 7/2002 | Roe et al. |
| 6,570,054 B1 | 5/2003 | Gatto et al. |
| 6,703,536 B2 | 3/2004 | Roe et al. |
| 6,710,223 B1 | 3/2004 | Rijswijck et al. |
| 6,716,441 B1 | 4/2004 | Osborne et al. |
| 6,716,805 B1 | 4/2004 | Sherry et al. |
| 6,793,930 B2 | 9/2004 | Gatto et al. |
| 6,803,496 B2 | 10/2004 | Elder et al. |
| 6,808,791 B2 | 10/2004 | Curro et al. |
| 6,878,433 B2 | 4/2005 | Curro et al. |
| 6,936,580 B2 | 8/2005 | Sherry et al. |
| 7,033,645 B2 | 4/2006 | Gatto et al. |
| 7,037,569 B2 | 5/2006 | Curro et al. |
| 7,166,292 B2 * | 1/2007 | Isele et al. ..................... 424/402 |
| 2002/0147433 A1 | 10/2002 | McOsker et al. |
| 2002/0165508 A1 | 11/2002 | Klofta et al. |
| 2004/0175343 A1 | 9/2004 | Osborne et al. |
| 2005/0113277 A1 | 5/2005 | Sherry et al. |
| 2005/0133174 A1 | 6/2005 | Gorley et al. |
| 2005/0153857 A1 | 7/2005 | Sherry et al. |
| 2006/0241554 A1 | 10/2006 | Elder et al. |

FOREIGN PATENT DOCUMENTS

| | | |
|---|---|---|
| EP | 0 297 828 A1 | 1/1989 |
| EP | 0 631 768 A1 | 1/1995 |
| EP | 0 692 263 B1 | 1/1996 |
| EP | 0882442 A1 * | 9/1998 |
| GB | 2033751 A | 5/1980 |
| JP | 61-028078 | 2/1986 |
| JP | 02-31756 | 2/1990 |
| JP | 05-285170 | 11/1993 |
| JP | 05-339880 | 12/1993 |
| JP | 08-52175 | 2/1996 |
| JP | 08-199476 A | 8/1996 |
| WO | WO 00/00026 A1 | 1/2000 |
| WO | WO 00/64502 A1 | 11/2000 |

* cited by examiner

TOP-BIASED BENEFICIAL COMPONENTS ON SUBSTRATES

CROSS-REFERENCE TO RELATED APPLICATION

This application is a continuation of U.S. application Ser. No. 09/895,027, filed Jun. 29, 2001 now U.S. Pat. No. 7,166,292, the substance of which is incorporated herein by reference.

FIELD OF THE INVENTION

The present invention relates to substrates that comprise a beneficial component deposited thereon. The beneficial component can comprise a variety of ingredients depending upon the intended use of the beneficial component treated substrate. The beneficial component is also Top-Biased on the substrate such that the ratio of the quantity of the beneficial component present on or within the top ⅓ of the substrate is at least about 2.2 times the quantity of the component within bottom ⅓ of the substrate until the time of the use of the article.

BACKGROUND OF THE INVENTION

Treated substrates which transfer a beneficial component to a target surface are well known in the art for a variety of applications on both animate and inanimate surfaces. Products comprising substrates can provide skin health benefits by delivering a skin care composition to the skin of the user. Such products include absorbent articles such as diapers, training pants, adult incontinence briefs, feminine hygiene products, and the like, which seek to deliver compositions to reduce diaper rash or diaper dermatitis in addition to irritations caused by the use of the absorbent article or to aid in the clean-up of body fecal waste. Other substrate products which may be used to deliver skin care compositions to the skin and/or hair of a user include facial tissues, toilet paper, cleansing implements, bandages, wound dressings, articles of clothing such as socks, wipes, and gloves. Alternatively, products comprising substrates can also be used to deliver cleansing, waxing, and/or polishing compositions to an inanimate target surface such as kitchen counters, floors, cars, furniture, etc. Such substrate products may include dusting or cleaning implements, wipes, scouring pads, sponges, and/or mops.

Currently, when beneficial components such as skin care compositions or cleansing, waxing and/or polishing compositions are applied to porous substrates (e.g., webs), much of the beneficial component is lost into the substrate, itself, which results in inefficient transfer of the beneficial component to a target surface. This results in a need to apply more of the beneficial component to the substrate and/or a lower transfer of the beneficial component to the desired animate or inanimate target surface.

U.S. Pat. No. 5,643,588 to Roe et al. addresses these concerns to some degree, relative to absorbent articles that are designed to deliver a skin protective material. In particular, Roe describes an absorbent article whose topsheet is surface treated with a lotion that comprises an emollient for facilitating easier cleaning of feces and other exudates and an agent which immobilizes the lotion so that it does not migrate from the point of initial application, particularly into the core of the diaper. However, despite the use of immobilizers, there are still problems associated with lotion migration, inasmuch as it penetrates the topsheet and there is some loss of lotion due to its migration through the topsheet.

Thus, it is desirable to provide products comprising substrates having a beneficial component disposed thereon wherein the beneficial component is biased in the Z direction (on or near the contacting surface).

It is also desirable to provide products wherein a Top-Biased beneficial component comprises skin conditioning components, hair conditioning components, cosmetic components, cleaning components, waxing components, and polishing components.

It is also desirable to provide products with a body contacting surface having a skin care composition disposed on at least a portion thereof wherein the skin care composition comprises multiple layers.

SUMMARY OF THE INVENTION

The present invention provides a substrate for improved transfer of a beneficial component to a target surface and methods for making the same. Particularly, the invention provides an article of manufacture having a contacting surface with a beneficial component that is transferred from the contacting surface to a target surface during use of the article. The beneficial component is formulated and/or applied to the article in such a way as to "Top-Bias" the component on or near the contacting surface of the article.

In one embodiment the article comprises a liquid permeable porous substrate having a contacting surface and an opposing surface disposed oppositely thereto, wherein the substrate has a thickness of "Z" as measured from the contacting surface to the opposing surface and a beneficial component releasably disposed on at least a portion of the contacting surface. In this embodiment, the ratio of the quantity of the beneficial component present on or within the thickness between 0 and Z/3 of the substrate is at least about 2.2 times the quantity of the component within the thickness between 2Z/3 and Z of the substrate until the time of the use of the article. Various approaches to achieving this "Top-Bias" are also described and claimed.

BRIEF DESCRIPTION OF THE DRAWINGS

While the specification concludes with claims particularly pointing out and distinctly claiming the present invention, it is believed that the present invention will be better understood from the following description in conjunction with the following drawings, in which like reference numbers identify identical elements and wherein:

DETAILED DESCRIPTION OF THE INVENTION

I. Definitions

As used herein, the term "comprising" means that the various components, ingredients, or steps can be conjointly employed in practicing the present invention. Accordingly, the term "comprising" encompasses the more restrictive terms "consisting essentially of" and "consisting of".

Figure 2:
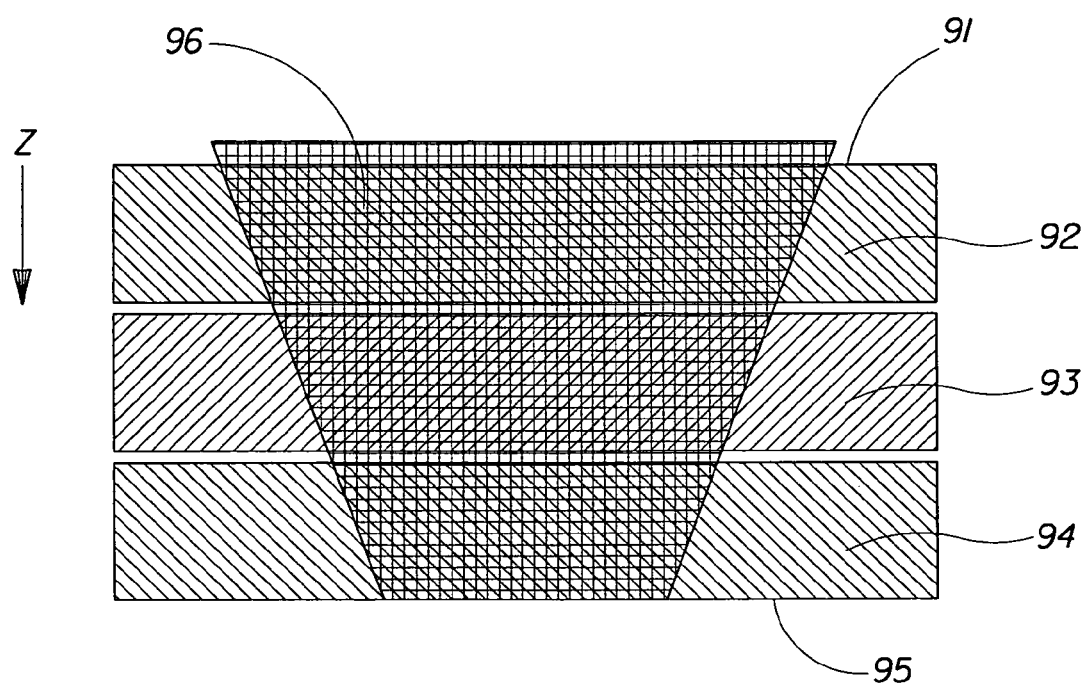
FIG. 2 is a cross-section view of a treated substrate having beneficial component disposed thereon in accordance with the present invention.

As used herein and illustrated in FIG. 2, the term "Top-Bias" means the ratio of the quantity of the beneficial component 96 present on or within the top ⅓ of the substrate 92 is at least about 2.2 times the quantity of the beneficial component 96 within the bottom ⅓ of the substrate 94. The middle ⅓ of the substrate 93 is between the top and bottom thirds. The "Z" direction is perpendicular to the contacting surface 91 of the substrate and is a convenient means for specifying the thickness of the substrate. For measurement purposes the contacting surface 91 is defined as Z=0 and the opposing surface 95 is defined as Z=Z. This is employed in determination of the Top-Bias of the lotion as described in the 'Methods—Measuring Top-Bias' section.

As used herein in describing the beneficial component, the term "lipophobic" refers to a component or distinct layer of the beneficial component which has a low affinity for lipids.

As used herein, "an absorbent article" means any absorbent article, including diapers, training pants, adult incontinence briefs, feminine hygiene products, bandages, breast pads, intra labial devices and the like, typically having a liquid impervious backsheet, a liquid pervious topsheet, and an absorbent core positioned between the topsheet and the backsheet.

As used herein, the phrase "contacting surface" of a substrate is one or more surfaces of the substrate that may contact the surface intended to benefit from the use of the substrate (animate or inanimate) at some time during use. When the substrate is part of an absorbent article, the contacting surface includes portions of the topsheet, leg cuffs, waist region, and side panels which contact the wearer's skin during use. When the substrate is part of a personal cleansing implement, the contacting surface may be a surface of a substrate opposite an exfoliating surface wherein the contacting surface is intended to deliver conditioning agents to skin after exfoliating with the non-treated side of the substrate. When the substrate is part of an inanimate object-cleaning implement, such as a mop, the contacting surface is the surface of the substrate which will contact inanimate object intended to be cleaned, such as a floor.

As used herein, the phrase "target surface" refers to an animate or inanimate surface to which the contacting surface transfers the beneficial component.

As used herein the phrase "releasably disposed" means that at least a portion of the beneficial component is transferred to the target surface during use.

As used herein, the phrase "animate surface" refers to skin or hair or teeth of something living. The term "inanimate surface" refers to any non-living surface including, but not limited to, the exterior of a car (e.g., paint surface), a floor, a wooden surface, a pot, dishes, appliances, decorative items and/or shoes.

As used herein, the phrase "solubility parameter" refers to the total sum of all attractive forces radiating out from a molecule with units of (calories/cubic centimeter)$^{1/2}$. Typical ranges of solubility parameter for beneficial components are 5 to 24 (calories/cubic centimeter)$^{1/2}$. For the purposes of the present invention, the solubility parameters for a given component are determined from standard tables or supplier information. Where table values are not readily available, solubility parameters can be calculated from tabulated values of the additive group contributions for the heat of vaporization and molar volume of the components of that compound, using the following equation:

$$\delta = \left[ \frac{\sum_i E_i}{\sum_i m_i} \right]^{1/2}$$

wherein $\Sigma_i E_i$=the sum of the heat of vaporization additive group contributions, and $\Sigma_i m_i$=the sum of the molar volume additive group contributions. Dispersed particles are not used in the determination of solubility parameter.

Standard tabulations of heat of vaporization and molar volume additive group contributions for a wide variety of atoms and groups of atoms are collected in Barton, A. F. M., *Handbook of Solubility Parameters*, CRC Press, Chapter 6, Table 3, pp. 64-66 (1985), which is incorporated by reference herein in its entirety. The above solubility parameter equation is described in Fedors, R. F., "A Method for Estimating Both the Solubility Parameters and Molar Volumes of Liquids", Polymer Engineering and Science, vol. 14, no. 2, pp. 147-154 (February 1974), which is incorporated by reference herein in its entirety.

Solubility parameters obey the law of mixtures such that the solubility parameter for a mixture of materials is given by the weighted arithmetic mean (i.e., the weighted average) of the solubility parameters for each component of that mixture. See, *Handbook of Chemistry and Physics*, 57th edition, CRC Press, p. C-726 (1976-1977), which is incorporated by reference herein in its entirety.

Solubility parameters have also been tabulated for a wide variety of chemical materials. Tabulations of solubility parameters are found in the above-cited Handbook of Solubility Parameters. Also, see "Solubility Effects In Product, Package, Penetration, And Preservation", C. D. Vaughan, Cosmetics and Toiletries, vol. 103, October 1988, pp. 47-69, which is incorporated by reference herein in its entirety.

With respect to the beneficial component(s), all percentages, ratios and proportions used herein are by weight in the final product such that volatile substances are not included unless otherwise specified. Other terms are defined herein where initially discussed.

II. Liquid Permeable, Porous Substrate

A. General Description of Embodiments

As used herein, the term "substrate" refers to any carrier material, preferably integral material, in the form of a sheet, pad, or the like, comprising a single layer or material or a composite or a laminate of two or more layers or materials upon which a beneficial component can be added. Substrates of the present invention may include any of a number of different materials useful in various products. For use in a diaper or other absorbent article, the substrate may be a nonwoven, a woven, a film, a foam, an elastic substrate, or combinations thereof. For example, preferred substrates may be comprised of cellulosic fibers, polyolefin such as polyethylenes, including linear low-density polyethylene (LLDPE), low density polyethylene (LDPE), ultra low-density polyethylene (ULDPE), high-density polyethylene (HDPE), or polypropylene and blends thereof with the above and other materials. Examples of other suitable polymeric materials which may be used include, but are not limited to, polyester, polyurethanes, compostable or bio-degradable polymers, heat shrink polymers, thermoplastic elastomers, metalycene catalyst-based polymers (e.g., Insite™ available from Dow Chemical and Exxact™ available from Exxon), and breathable polymers. The substrate may also be comprised of a synthetic woven, synthetic knit, nonwoven, apertured film, macroscopically expanded three-dimensional formed films, absorbent or fibrous absorbent materials, open celled foams, filled compositions, or laminates and/or combinations thereof.

Other substrates useful in the present invention are described in U.S. Pat. No. 6,060,149, issued to Nissing et al., entitled "Multiple Layer Wiping Articles", which is incorporated herein by reference in its entirety. Also useful are substrates described in: co-pending U.S. Ser. No. 09/584,676, filed on May 31, 2000, in the names of Curro et al., entitled "Laminate Web"; U.S. Ser. No. 09/553,871, filed on Apr. 20, 2000, in the names of Dye et al., entitled "Disposable Article Comprising an Apertured Laminate Web"; co-pending U.S. Ser. No. 09/553,641, filed on Apr. 20, 2000, entitled "Disposable Article Comprising an Apertured Laminate Web" in the names of Dye et al.; PCT Publication No. WO 00/00026 and U.S. Ser. No. 09/719,268, filed on Jun. 14, 1999, in the names of Self et al., entitled "Method of Obtaining Effective Residual Antimicrobial Activity and Premoistened Wipe Thereof" and co-pending U.S. Ser. No. 09/671,718, filed on Sep. 27, 2000, in the names of Sherry et al., entitled "Hard Surface Cleaning Compositions, Premoistened Wipes, Methods of Use, and Articles Comprising Said Compositions for Wipes and Instructions for Use, Resulting in Easier Cleaning and Maintenance, Improved Surface Appearance and/or Hygiene Under Stress Conditions Such As No-Rinse," each of which is incorporated herein by reference in its entirety. One suitable airlaid nonwoven substrate for use in the present invention is the airlaid nonwoven substrate employed in PAMPERS® BABY FRESH brand baby wipes marketed by The Procter & Gamble Co. of Cincinnati, Ohio. The "substrate" may also be in the form of a cotton ball, tissue, foam applicator, scouring pad, sponge, or any other flexible dispensing means capable of delivering beneficial components as described herein when used in accordance with the present invention.

In one embodiment of the present invention, the substrate is extensible in at least one direction. In addition, the substrates may have one or more discrete zones of extensibility. The substrate may be elastically extensible. The substrate may comprise an elastic material operatively joined to one or more inelastic components in an elastically contractible condition such as described in U.S. Pat. No. 3,860,003 issued to Buell on Jan. 14, 1975, and U.S. Pat. No. 6,198,018, issued to Curro on Mar. 6, 2001, which is incorporated herein by reference.

B. Specific Embodiments Utilizing Webs

A "unitary" absorbent article refers to absorbent articles which are formed of separate parts united together to form a coordinated entity so that they do not require separate manipulative parts like a separate holder and/or liner. A preferred embodiment of an absorbent article of the present invention is the unitary disposable absorbent article, diaper 20, shown in FIG. 1. As used herein, the term "diaper" refers to an absorbent article generally worn by infants and incontinent persons about the lower torso. The present invention is also applicable to other absorbent articles such as incontinence briefs, incontinence undergarments, absorbent inserts, breast pads, inter labial devices, diaper holders and liners, feminine hygiene garments, wipes, mops, bandages and the like.

Figure 1:
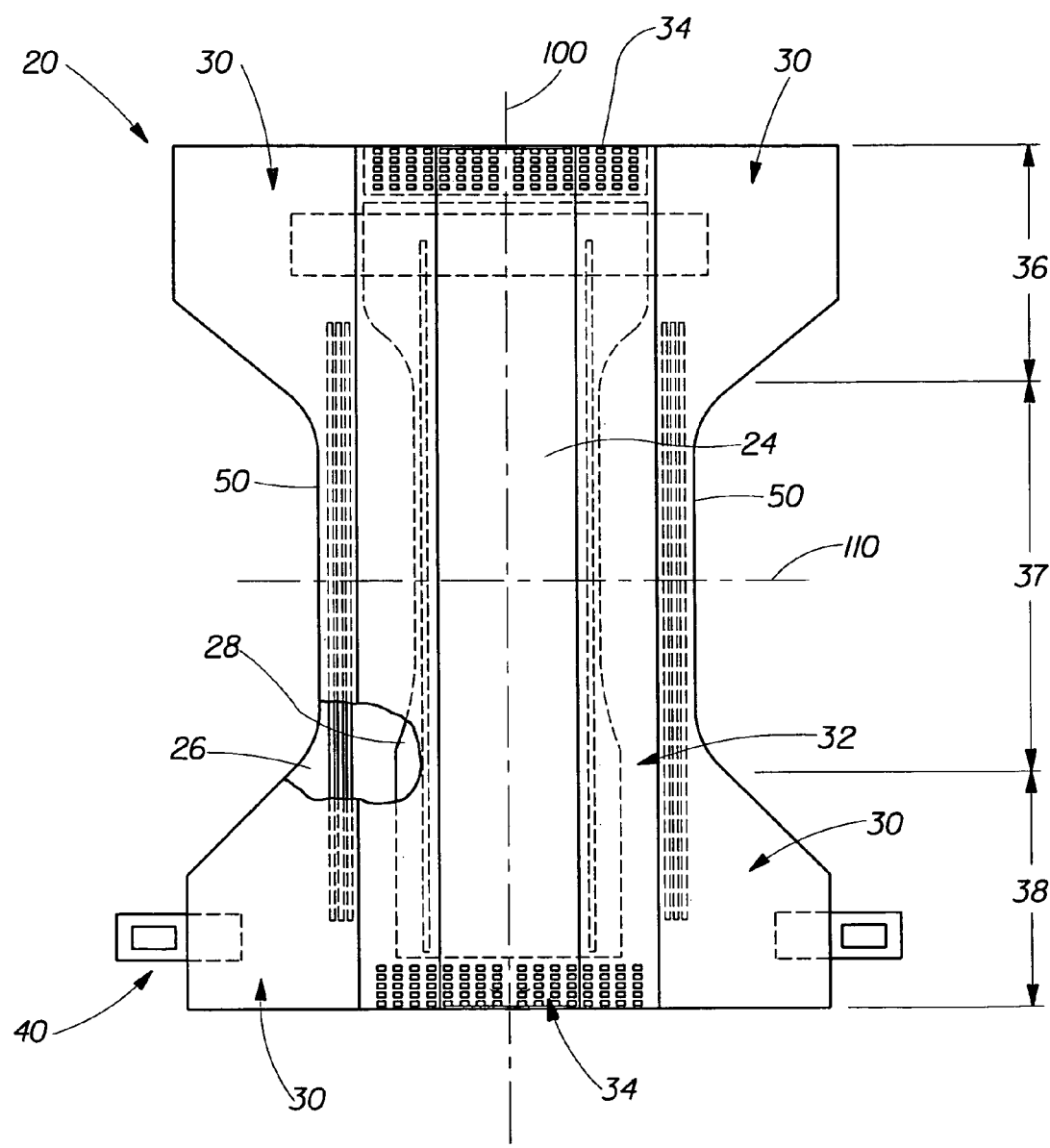
FIG. 1 plan view of an absorbent article in the form of a diaper according to the present invention.

FIG. 1 is a plan view of the diaper 20 of the present invention in a flat-out, state with portions of the structure being cut-away to more clearly show the construction of the diaper 20. The portion of the diaper 20 which faces the wearer is oriented towards the viewer. As shown in FIG. 1, the diaper 20 preferably comprises a liquid pervious topsheet 24; a liquid impervious backsheet 26; an absorbent core 28 which is preferably positioned between at least a portion of the topsheet 24 and the backsheet 26; side panels 30; elasticized leg cuffs 32; an elastic waist feature 34; and a fastening system generally designated 40. The diaper 20 is shown in FIG. 1 to have a first waist region 36, a second waist region 38 opposed to the first waist region 36 and a crotch region 37 located between the first waist region 36 and the second waist region 38. The periphery of the diaper 20 is defined by the outer edges of the diaper 20 in which longitudinal edges 50 run generally parallel to the longitudinal centerline 100 of the diaper 20 and end edges 52 run between the longitudinal edges 50 generally parallel to the lateral centerline 110 of the diaper 20.

The topsheet 24 is preferably positioned adjacent to the body surface of the absorbent core 28 and may be joined thereto and/or to the backsheet 26 by any attachment means known in the art. Suitable attachment means are described above with respect to means for joining the backsheet 26 to other elements of the diaper 20. In one preferred embodiment of the present invention, the topsheet 24 and the backsheet 26 are joined directly to each other in some locations and are indirectly joined together in other locations by directly joining them to one or more other elements of the diaper 20. The topsheet 24 is preferably compliant, soft feeling, and non-irritating to the wearer's skin. Further, at least a portion of the topsheet 24 is liquid pervious, permitting liquids to readily penetrate through its thickness. A suitable topsheet may be manufactured from a wide range of materials, such as porous foams, reticulated foams, apertured plastic films, or woven or nonwoven materials of natural fibers (e.g., cellulosic, wood or cotton fibers), synthetic fibers (e.g., polyester or polypropylene fibers), or a combination of natural and synthetic fibers. One suitable topsheet 24 comprising a web of staple-length polypropylene fibers is manufactured by Veratec, Inc., a Division of International Paper Company, of Walpole, Mass. under the designation P-8.

Suitable formed film topsheets are described in U.S. Pat. No. 3,929,135, entitled "Absorptive Structures Having Tapered Capillaries" issued to Thompson on Dec. 30, 1975; U.S. Pat. No. 4,324,246 entitled "Disposable Absorbent Article Having A Stain Resistant Topsheet" issued to Mullane, et al. on Apr. 13, 1982; U.S. Pat. No. 4,342,314 entitled "Resilient Plastic Web Exhibiting Fiber-Like Properties" issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression" issued to Ahr, et al. on Jul. 31, 1984; and U.S. Pat. No. 5,006,394 "Multilayer Polymeric Film" issued to Baird on Apr. 9, 1991. Other suitable topsheets 24 may be made in accordance with U.S. Pat. Nos. 4,609,518 and 4,629,643 issued to Curro et al. on Sep. 2, 1986 and Dec. 16, 1986, respectively, and both of which are incorporated herein by reference. Such formed films are available from The Procter & Gamble Company of Cincinnati, Ohio as "DRI-WEAVE" and from Tredegar Corporation of Terre Haute, Ind. as "CLIFF-T."

Preferably, at least a portion of the topsheet 24 is made of a hydrophobic material or is treated to be hydrophobic in order to isolate the wearer's skin from liquids contained in the absorbent core 28. If the topsheet 24 is made of a hydrophobic material, preferably at least a portion of the upper surface of the topsheet 24 is treated to be hydrophilic so that liquids will transfer through the topsheet more rapidly. The topsheet 24 can be rendered hydrophilic by treating it with a surfactant or by incorporating a surfactant into the topsheet. The resulting treated topsheet has both hydrophilic and lipophilic characteristics which enhances wicking of body wastes.

Another disposable absorbent article for use in the present invention is an incontinence article. The term "incontinence article" refers to pads, undergarments (pads held in place by a suspension system of some type, such as a belt, or the like), inserts for absorbent articles, capacity boosters for absorbent articles, briefs, bed pads, and the like regardless of whether they are worn by adults or other incontinent persons. Suitable incontinence articles are disclosed in U.S. Pat. No. 4,253,461 issued to Strickland, et al. on Mar. 3, 1981; U.S. Pat. Nos. 4,597,760 and 4,597,761 issued to Buell on Jul. 1, 1986; the above-mentioned U.S. Pat. No. 4,704,115; U.S. Pat. No. 4,909,802 issued to Ahr, et al. on Apr. 16, 1987; U.S. Pat. No. 4,964,860 issued to Gipson, et al. on Oct. 23, 1990; and in U.S. Pat. No. 5,304,161, issued in the name of Noel, et al. on Apr. 19, 1994. The disclosures of each of these references are incorporated herein by reference.

Another disposable absorbent article for use in the present invention is a feminine hygiene article, such as a sanitary napkin. Suitable feminine hygiene articles are disclosed in U.S. Pat. No. 4,556,146, issued to Swanson et al. on Dec. 3, 1985; U.S. Pat. No. 4,589,876, issued to Van Tilburg on Apr. 27, 1993; U.S. Pat. No. 4,687,478, issued to Van Tilburg on Aug. 18, 1997; U.S. Pat. No. 4,950,264, issued to Osborn, III on Aug. 21, 1990; U.S. Pat. No. 5,009,653, issued to Osborn, III on Apr. 23, 1991; U.S. Pat. No. 5,267,992, issued to Van Tilburg on Dec. 7, 1993; U.S. Pat. No. 5,389,094, issued to Lavash et al. on Feb. 14, 1995; U.S. Pat. No. 5,413,568; issued to Roach et al. on May 9, 1995; U.S. Pat. No. 5,460,623, issued to Emenaker et al. on Oct. 24, 1995; U.S. Pat. No. 5,489,283, issued Van Tilburg on Feb. 6, 1996; U.S. Pat. No. 5,569,231, issued to Emenaker et al. on Oct. 29, 1996; and U.S. Pat. No. 5,620,430, issued to Bamber on Apr. 15, 1997, the disclosures of each of which are incorporated by reference herein.

III. Beneficial Component

The beneficial component of the present invention is a component deposited on a substrate in accordance with the present invention, which is transferred to the desired animate or inanimate target surface via the treated substrate upon contact with the surface during use. As such, the beneficial component may comprise ingredients known for use on absorbent articles and/or in areas such as personal care and household care. The beneficial component may comprise ingredients in one or more of the following categories: conditioning components, cleansing agents (for animate or inanimate objects), cosmetic components, and waxing and/or polishing/dusting compositions, and optional ingredients. When used in the present invention, the treated substrates typically comprise from about 1% to about 1000%, more preferably, from about 2% to about 500%, and most preferably from about 5% to about 250%, by weight of the substrate, of a beneficial component.

A. Conditioning Component

The conditioning component is used to improve and/or maintain healthy skin and/or hair of the wearer or user of the article incorporating the treated substrate (the treated substrate itself may also be the article). The conditioning component may also provide other therapeutic benefits to the skin and/or hair including but not limited to softening, soothing, coating, lubricating, or moisturizing.

Nonlimiting examples of conditioning agents include petroleum based emollients such as mineral oil, paraffins, petrolatum, wax and wax derivatives, silicone and silicone derivatives, lecithin, hydrogenated lecithin, lanolin, lanolin derivatives, $C_4$-$C_{40}$ strait and branched chain hydrocarbons, $C_1$-$C_{40}$ alcohol esters of $C_1$-$C_{40}$ carboxylic acids, $C_1$-$C_{40}$ alcohol esters of $C_2$-$C_{40}$ dicarboxylic acids, monoglycerides of $C_1$-$C_{40}$ carboxylic acids, diglycerides of $C_1$-$C_{40}$ carboxylic acids, triglycerides of $C_1$-$C_{40}$ carboxylic acids, ethylene glycol monoesters of $C_1$-$C_{40}$ carboxylic acids, ethylene glycol diesters of $C_1$-$C_{40}$ carboxylic acids, propylene glycol monoesters of $C_1$-$C_{40}$ carboxylic acids, propylene glycol diesters of $C_1$-$C_{40}$ carboxylic acids, $C_1$-$C_{40}$ carboxylic acid monoesters and polyesters of sugars, cylcomethicones having 3 to 9 silicon atoms, vegetable oils, hydrogenated vegetable oils, and combinations thereof.

Also useful are various $C_1$-$C_{40}$ monoesters and polyesters of sugars and related materials. These esters are derived from a sugar or polyol moiety and one or more carboxylic acid moieties. Depending on the constituent acid and sugar, these esters can be in either liquid or solid form at room temperature. The ester materials are further described in, U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977, U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985; each of which is incorporated by reference herein in its entirety.

Nonvolatile silicones such as polydialkylsiloxanes, polydiarylsiloxanes, and polyalkylarylsiloxanes are also useful oils. These silicones are disclosed in U.S. Pat. No. 5,069,897, to Orr, issued Dec. 3, 1991, which is incorporated by reference herein in its entirety. Commercially available polyalkylsiloxanes include the polydimethylsiloxanes, which are also known as dimethicones, nonlimiting examples of which include those sold by General Electric Company and the Dow Corning Corporation. Also useful herein are dimethiconols, which are hydroxy terminated dimethyl silicones. Commercially available dimethiconols are typically sold as mixtures with dimethicone or cyclomethicone (e.g., Dow Corning® 1401, 1402, and 1403 fluids). Also useful herein are polyalkylaryl siloxanes, such as polymethylphenyl silicones. These materials are available, for example, as SF 1075 methylphenyl fluid (sold by General Electric Company) and 556 Cosmetic Grade phenyl trimethicone fluid (sold by Dow Corning Corporation). Alkylated silicones such as methyldecyl silicone and methyloctyl silicone are useful herein and are commercially available from General Electric Company. Also useful herein are alkyl-modified siloxanes such as alkyl methicones and alkyl dimethicones wherein the alkyl chain contains 10 to 50 carbons. Such siloxanes are commercially available under the tradenames ABIL WAX 9810 ($C_{24}$-$C_{28}$ alkyl methicone) (sold by Goldschmidt), SF1632 (cetearyl methicone)(sold by General Electric Company) and AMS-C30 (sold by Dow Corning).

Other conditioning agents which may be useful in the present invention, and often will be relatively hydrophilic as compared to the above mentioned conditioning agents, include but are not limited to those selected from the group consisting of polyhydric alcohols, polypropylene glycols, polyethylene glycols, ureas, pyrolidone carboxylic acids, ethoxylated and/or propoxylated $C_2$-$C_{10}$ diols and triols, alpha-hydroxy $C_2$-$C_{22}$ carboxylic acids, ethoxylated and/or propoxylated sugars, polyacrylic acid copolymers, sugars having up to about 12 carbons atoms, sugar alcohols having up to about 12 carbon atoms, and mixtures thereof. Specific examples of useful hydrophilic conditioning agents include materials such guanidine; glycolic acid and glycolate salts (e.g., ammonium and quaternary alkyl ammonium); lactic acid and lactate salts (e.g., ammonium and quaternary alkyl ammonium); citric acid and citric acid salts; sucrose, fructose, glucose, eruthrose, erythritol, sorbitol, mannitol, glycerol, triacetin, hexanetriol, propylene glycol, butylene glycol, hexylene glycol, and the like; alkoxylated glucose; hyaluronic acid; cationic skin conditioning polymers (e.g., quaternary ammonium polymers such as Polyquaternium polymers); and mixtures thereof. Also useful are materials such as aloe vera in any of its variety of forms (e.g., aloe vera gel), chamomile, bisabolol, panthanol, vitamin E and its derivatives, chitosan and chitosan derivatives, e.g., chitosan lactate, lactamide monoethanolamine; acetamide monoethanolamine; and mixtures thereof. Also useful are propoxylated glycerols as described in U.S. Pat. No. 4,976,953, to Orr et al., issued Dec. 11, 1990, which is incorporated by reference herein in its entirety.

Additionally, the conditioning component may also be specially formulated to reduce the adherence of feces to skin (e.g., to improve the ease of bowel movement clean up) or to provide a skin/feces barrier function (e.g., to coat the skin to prevent the adherence of feces). Compositions useful for this purpose, particularly for use in absorbent articles, include liquid polyol polyesters comprising a polyhydric alcohol containing at least 4 hydroxyl groups esterified with fatty acid or other organic radicals having at least 2 carbon atoms and up to 30 carbon atoms which are described in greater detail in U.S. Pat. No. 5,607,760, issued on Mar. 4, 1997 to Roe, entitled "Disposable Absorbent Article having a Lotioned Topsheet Containing an Emollient and a Polyol Polyester Immobilizing Agent" which is incorporated by reference herein in its entirety. Other suitable compositions for this purpose include petroleum-based, fatty acid ester type, alkyl ethoxylate type, fatty acid ester ethoxylates, fatty alcohol type, and polysiloxane type emollients which are described in greater detail in U.S. Pat. No. 5,968,025, issued on Oct. 19, 1999 to Roe, et. al, entitled "Absorbent Article Having a Lotioned Topsheet", which is incorporated by reference herein in its entirety. Skin care compositions suitable for use in the present invention are described in co-pending U.S. patent application Ser. Nos. 08/926,532 and 08/926,533, each filed on Sep. 10, 1997; U.S. patent application Ser. Nos. 09/041,509, 09/041,232 and 09/041,266, each filed on Mar. 12, 1998; U.S. patent application Ser. No. 09/563,638, filed on May 2, 2000; U.S. Pat. No. 5,607,760 issued Mar. 4, 1997; U.S. patent application Ser. No. 09/466,343, filed on Dec. 17, 1999; U.S. Pat. No. 5,609,587 issued Mar. 11, 1997; U.S. Pat. No. 5,635,191 issued Jun. 3, 1997; U.S. Pat. No. 5,643,588 issued Jul. 1, 1997; and U.S. Pat. No. 6,153,209 issued Nov. 28, 2000; the disclosures of which are hereby incorporated by reference.

The conditioning component may also comprise structured conditioning agents. Suitable structured conditioning agents include, but are not limited to, vesicular structures such as ceramides, liposomes, and the like. In another embodiment, the conditioning components are comprised within a coacervate-forming composition. Suitable coacervate-forming compositions are described in greater detail in co-pending U.S. Ser. No. 09/553,641, filed on Apr. 20, 2000, in the names of Dye et al., entitled "Disposable Article Comprising an Apertured Laminate Web", which is incorporated herein by reference in its entirety.

The beneficial component may be in liquid or semi-solid form to allow for better processability (e.g., the material should be flowable under shear). Any liquid lotion form including, but not limited to, emulsions (e.g., course-emulsions, micro-emulsions, liquid-crystal systems, liposomes), dispersions/suspensions, pure solutions, semisolids (e.g., gels, waxes, hot melts), and the like would be suitable.

The beneficial component may be an emulsion. For instance, oil-in-water, water-in-oil, water-in-oil-in-water, and oil-in-water-in-silicone emulsions are useful herein. As used in the context of emulsions and phases, "water" may refer not only to water but also water soluble or polar agents like glycerin or polyethylene glycol.

The beneficial component, especially the conditioning component, of the present invention that is in emulsion form will preferably further contain from about 1 to about 30% and more preferably from about 2% to about 20% and still more preferably from about 3% to 10% of an emulsifier (i.e., a surfactant), based on the weight of beneficial component. Emulsifiers may be nonionic, anionic or cationic. Suitable emulsifiers are disclosed above as well as in U.S. Pat. No. 3,755,560, issued Aug. 28, 1973, Dickert et al.; U.S. Pat. No. 4,421,769, issued Dec. 20, 1983, Dixon et al.; and *McCutcheon's Detergents and Emulsifiers*, North American Edition, pages 317-324 (1986).

The beneficial component may also be in the form of a microemulsion. As used herein, "microemulsion" refers to thermodynamic stable mixtures of two immiscible solvents (one non-polar and the other polar) stabilized by an amphiphilic surfactant molecule. Preferred microemulsions include water-in-oil microemulsions.

Alternatively, the beneficial component may be in the form of a single phase such as an oil phase or a water phase. The beneficial component may also comprise two separate incompatible/immiscible phases, which form layers rather than emulsifying together. This is described in greater detail below in the Support Layer Approach. It is to be understood, however, that either or both of the critical layers in that approach could take any of the above mentioned forms (e.g., emulsions, microemulsions, phases, and mixtures thereof).

Suitable for use in the beneficial components intended for use on animate objects are cleansing agents, which typically comprise surfactants and cleaning solvents.

Surfactants:

When used in the present invention as a cleaning agent component, the weight of the surfactants comprise from about 1% to about 1,000%, preferably from about 5% to about 500%, and more preferably from about 10% to about 250%, based on the weight of the substrate.

The surfactants of the cleansing agent may be lathering surfactants. A wide variety of lathering surfactants are useful herein and include those selected from the group consisting of anionic lathering surfactants, nonionic lathering surfactants, cationic lathering surfactants, amphoteric lathering surfactants, and mixtures thereof.

Anionic Lathering Surfactants:

Nonlimiting examples of anionic lathering surfactants useful in the cleansing agents used in the beneficial component are disclosed in McCutcheon's, *Detergents and Emulsifiers*, North American edition (1986), published by Allured Publishing Corporation; McCutcheon's, *Functional Materials*, North American Edition (1992); and U.S. Pat. No. 3,929,678, to Laughlin et al., issued Dec. 30, 1975, each of which is incorporated by reference herein in their entirety. A wide variety of anionic surfactants are potentially useful herein. Nonlimiting examples of anionic lathering surfactants include those selected from the group consisting of alkyl and alkyl ether sulfates, sulfated monoglycerides, sulfonated olefins, alkyl aryl sulfonates, primary or secondary alkane sulfonates, sodium dialkyl sulfosuccinates, acyl taurates, acyl isethionates, alkyl glycerylether sulfonate, sulfonated methyl esters, sulfonated fatty acids, alkyl phosphates, ethoxylated alkyl phosphates, acyl glutamates, acyl sarcosinates, alkyl sulfoacetates, acylated peptides, alkyl ether carboxylates, acyl lactylates, anionic fluorosurfactants, and combinations thereof.

Nonionic Lathering Surfactants:

Nonlimiting examples of nonionic lathering surfactants useful in the present invention are disclosed in McCutcheon's, *Detergents and Emulsifiers*, North American edition (1986), published by allured Publishing Corporation; and McCutcheon's, *Functional Materials*, North American Edition (1992); both of which are incorporated by reference herein in their entirety. Nonionic lathering surfactants useful herein include those selected from the group consisting of alkyl glucosides, alkyl polyglucosides, polyhydroxy fatty acid amides, alkoxylated fatty acid esters, sucrose esters, amine oxides, and mixtures thereof.

Cationic Lathering Surfactants:

Cationic lathering surfactants are also useful in cleansing agents used in the present invention. Suitable cationic lathering surfactants include, but are not limited to, fatty amines, di-fatty quaternary amines, tri-fatty quaternary amines, imidazolinium quaternary amines, and combinations thereof. Nonionic surfactants have been found to be particularly useful in combination with such cationic lathering surfactants.

Amphoteric Lathering Surfactants:

The term "amphoteric lathering surfactant," as used herein, is also intended to encompass zwitterionic surfactants, which are well known to formulators skilled in the art as a subset of amphoteric surfactants. A wide variety of amphoteric lathering surfactants can be used in the cleansing agent of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate. Nonlimiting examples of amphoteric surfactants useful in the component of the present invention are disclosed in McCutcheon's, *Detergents and Emulsifiers*, North American edition (1986), published by allured Publishing Corporation; and McCutcheon's, *Functional Materials*, North American Edition (1992); both of which are incorporated by reference herein in their entirety. Nonlimiting examples of amphoteric or zwitterionic surfactants are those selected from the group consisting of betaines, sultaines, hydroxysultaines, alkyliminoacetates, iminodialkanoates, aminoalkanoates, and mixtures thereof. Each of these types of surfactants is described in greater detail in copending U.S. Ser. No. 09/553,641, filed on Apr. 20, 2000, in the names of Dye et al., entitled "Disposable Article Comprising an Apertured Laminate Web", which is incorporated herein by reference in its entirety.

Organic Cleaning Solvent:

Such solvents typically have a terminal $C_3$-$C_6$ hydrocarbon attached to from one to three ethylene glycol or propylene glycol moieties to provide the appropriate degree of hydrophobicity and, preferably, surface activity. Examples of commercially available cleaning solvents based on ethylene glycol chemistry include mono-ethylene glycol n-hexyl ether (Hexyl Cellosolve® available from Union Carbide). Examples of commercially available cleaning solvents based on propylene glycol chemistry include the di-, and tri-propylene glycol derivatives of propyl and butyl alcohol, which are available from Arco Chemical, 3801 West Chester Pike, Newtown Square, Pa. 19073) and Dow Chemical (1691 N. Swede Road, Midland, Mich.) under the trade names Arcosolv® and Dowanol®. Solvents may be selected from the group consisting of mono-propylene glycol mono-propyl ether, di-propylene glycol mono-propyl ether, mono-propylene glycol mono-butyl ether, di-propylene glycol mono-propyl ether, di-propylene glycol mono-butyl ether; tri-propylene glycol mono-butyl ether; ethylene glycol mono-butyl ether; di-ethylene glycol mono-butyl ether, ethylene glycol mono-hexyl ether and di-ethylene glycol mono-hexyl ether, and mixtures thereof. "Butyl" includes both normal butyl, isobutyl and tertiary butyl groups. Mono-propylene glycol and mono-propylene glycol mono-butyl ether are the most preferred cleaning solvent and are available under the tradenames Dowanol DPnP® and Dowanol DPnB®. Di-propylene glycol mono-t-butyl ether is commercially available from Arco Chemical under the tradename Arcosolv PTB®.

B. Cosmetic Components

Cosmetic components that are suitable for inclusion into the present article include foundations, blushes, blemish covering compositions, opacifying agents, tints, and other typical cosmetic coloring products. Such components, in effect, result in an article of the present invention that is suitable for make-up application.

C. Cleaning Component

For household care uses, the beneficial component of the present invention is suitable for providing cleaning benefits of household areas, e.g., target hard surfaces such as counter tops, walls, basins, tubs, floors, windows, etc. Such beneficial components are hereafter referred to as cleaning components. Preferably, such cleaning components are liquids since they can be easily applied to surfaces in a neat and concentrated manner to the soiled area. Solid cleaning components are, however, also acceptable so long as they are dissolved or suspended in a water or another liquid upon use. Preferably, the cleaning components of the present invention comprise a safe and effective amount of a polymer that renders the target surface hydrophilic. This increase in hydrophilicity provides improved final appearance by providing "sheeting" of the water from the surface and/or spreading of the water on the surface, and this effect is preferably seen when the surface is rewetted and even when subsequently dried after the rewetting.

In the context of floor, counter, wall, etc. applications, a class of preferred nonionic surfactant is alkyl ethoxylates. The alkyl ethoxylates of the present invention are either linear or branched, and contain from about 8 carbon atoms to about 14 carbon atoms, and from about 4 ethylene oxide units to about 25 ethylene oxide units. Examples of alkyl ethoxylates include Neodol® 91-6, Neodol 91-8® supplied by the Shell Corporation (P.O. Box 2463, 1 Shell Plaza, Houston, Tex.), and Alfonic® 810-60 supplied by Vista Corporation, (900 Threadneedle P.O. Box 19029, Houston, Tex.).

The liquid cleaning components according to the present invention are prepared with relatively low levels of active. Typically, such cleaning components will comprise sufficient surfactant and optional solvent, as discussed hereinafter, to be effective as hard surface cleaners yet remain economical; accordingly they typically contain from about 0.005% to about 0.5% by weight of the beneficial composition of surfactant, preferably alkylpolyglycoside and/or $C_{8-14}$ alkylethoxylate surfactant, more preferably from about 0.01% to about 0.4% surfactant, and even more preferably from about 0.01% to about 0.3% surfactant. It has been found that use of low, rather than high levels of surfactant are advantageous to overall end result performance. Additionally, cleaning agents include impalpable particulate/abrasive type materials like pumice, kaolin, zinc oxide, starch, talc, titanium dioxide, silicone particles, Teflon®, etc., having a particle size in the range of about 1 to 100 microns may be used Some non-limiting examples of homopolymers and copolymers which can be used as water soluble polymers of the present invention are: adipic acid/dimethylaminohydroxypropyl diethylenetriamine copolymer; adipic acid/epoxypropyl diethylenetriamine copolymer; polyvinyl alcohol; methacryloyl ethyl betaine/methacrylates copolymer; ethyl acrylate/methyl methacrylate/methacrylic acid/acrylic acid copolymer; polyamine resins; and polyquaternary amine resins; poly(ethenylformamide); poly(vinylamine) hydrochloride; poly(vinyl alcohol-co-6% vinylamine); poly(vinyl alcohol-co-12% vinylamine); poly(vinyl alcohol-co-6% vinylamine hydrochloride); and poly(vinyl alcohol-co-12% vinylamine hydrochloride). Preferably, said copolymer and/or homopolymers are selected from the group consisting of adipic acid/dimethylaminohydroxypropyl diethylenetriamine copolymer; poly(vinylpyrrolidone/dimethylaminoethyl methacrylate); polyvinyl alcohol; ethyl acrylate/methyl methacrylate/methacrylic acid/acrylic acid copolymer; methacryloyl ethyl betaine/methacrylates copolymer; polyquaternary amine resins; poly(ethenylformamide); poly(vinylamine) hydrochloride; poly(vinyl alcohol-co-6% vinylamine); poly(vinyl alcohol-co-12% vinylamine); poly (vinyl alcohol-co-6% vinylamine hydrochloride); and poly (vinyl alcohol-co-12% vinylamine hydrochloride).

Polymers useful in the cleaning component of the present invention can be selected from the group consisting of copolymers of hydrophilic monomers. The polymer can be linear random or block copolymers, and mixtures thereof. The term "hydrophilic" is used herein consistent with its standard meaning of having affinity for water.

Nonlimiting examples of useful hydrophilic monomers are unsaturated organic mono- and polycarboxylic acids, such as acrylic acid, methacrylic acid, crotonic acid, maleic acid and its half esters, itaconic acid; unsaturated alcohols, such as vinyl alcohol, allyl alcohol; polar vinyl heterocyclics, such as, vinyl caprolactam, vinyl pyridine, vinyl imidazole; vinyl amine; vinyl sulfonate; unsaturated amides, such as acrylamides, e.g., N,N-dimethylacrylamide, N-t-butyl acrylamide; hydroxyethyl methacrylate; dimethylaminoethyl methacrylate; salts of acids and amines listed above; and the like; and mixtures thereof. Some preferred hydrophilic monomers are acrylic acid, methacrylic acid, N,N-dimethyl acrylamide, N,N-dimethyl methacrylamide, N-t-butyl acrylamide, dimethylamino ethyl methacrylate, thereof, and mixtures thereof.

Nonlimiting examples of polymers for use in the present invention include the following: poly(vinyl pyrrolidone/acrylic acid) sold under the name "Acrylidone"® by ISP and poly(acrylic acid) sold under the name "Accumer"® by Rohm & Haas. Other suitable materials include sulfonated polystyrene polymers sold under the name Versaflex® sold by National Starch and Chemical Company, especially Versaflex 7000.

The level of polymeric material will normally be less than about 0.5%, preferably from about 0.01% to about 0.4%, more preferably from about 0.01% to about 0.3%, by weight of the beneficial composition.

Preferred polymers in the cleaning component are selected from the group consisting of polystyrene sulfonate; polyvinyl pyrrolidone; polyvinyl pyrrolidone acrylic acid copolymer; polyvinyl pyrrolidone acrylic acid copolymer sodium salt; polyvinyl pyrrolidone acrylic acid copolymer potassium salt; polyvinyl pyrrolidone-vinyl imidazoline; polyvinyl pyridine; polyvinyl pyridine n-oxide; and combinations thereof. A preferred polymer is polyvinyl pyridine n-oxide.

In addition to the above ingredients, the cleaning component may optionally comprise a cationic surfactant, anionic surfactant, amphoteric surfactant, bleaching agent, preferably hydrogen peroxide. Other optional ingredients include mild acids such as citric and acetic acid are also useful in the cleaning component as they can dissolve inorganic materials as well as soap scum type stains due to their pH lowering effect. In addition, some of these weak acids can sesquester calcium and magnesium, which leads to improved surfactant/emulsifier performance. Finally, some weak organic acids can act as anti-microbials. There is also a skin exfoliation effect used in alpha hydroxy acid cosmetics. Additionally, chelators, such as ethylenediaminetetraacetic acid are effective in sequestering calcium and magnesium hardness to enhance the effectiveness of the cleaning surfactant system, as they are effective in removing calcium/magnesium soap scums due to their ability to sequester calcium/magnesium and solubilize the metal soap scum.

D. Waxing and/or Polishing Compositions

The beneficial component of the presently disclosed articles may comprise a polishing/waxing composition where the desired benefit is to deposit a wax and/or polish to an inanimate surface such as cars, shoes, floors, counters, furniture, wood, and/or walls. Such additives are preferably applied to the article at an add-on level of 0.1 to 100 grams per square meter. Waxing and/or polishing compositions may comprise materials selected from the group consisting of a wax, oil, and combinations thereof. Suitable waxes include various types of hydrocarbons, as well as esters of certain fatty acids (e.g., saturated triglycerides) fatty alcohols, and silicones and functionalized silicones. They can be derived from natural sources (i.e., animal, vegetable or mineral) or can be synthesized. Mixtures of these various waxes can also be used. Some representative animal and vegetable waxes that can be used in the present invention include beeswax, carnauba, spermaceti, lanolin, shellac wax, candelilla, and the like. Representative waxes from mineral sources that can be used in the present invention include petroleum-based waxes such as paraffin, petrolatum and microcrystalline wax, and fossil or earth waxes such as white ceresine wax, yellow ceresine wax, white ozokerite wax, and the like. Representative synthetic waxes that can be used in the present invention include polyethylene wax, chlorinated naphthalenes such as "Halowax," hydrocarbon type waxes made by Fischer-Tropsch synthesis, and the like. Other preferred polishing/dusting components are supplied as mixtures of wax and oil, such as petrolatum.

A preferred waxing and/or polishing/dusting composition comprises a mixture of a wax and mineral oil, as it enhances the ability of the article to pick up and retain particulate material from surfaces, while minimizing the amount of residue left on the surface being wiped with the article. When a mixture of mineral oil and wax is utilized, the components will preferably be mixed in a weight ratio of oil to wax of from about 1:99 to about 7:3, more preferably from about 1:99 to about 3:2, still more preferably from about 1:99 to about 2:3, by weight. In a particularly preferred embodiment, the ratio of oil to wax is about 1:1, by weight, and the additive is applied at an add-on level of about 5%, by weight. A preferred mixture for the polishing/dusting component is a 1:1 mixture of mineral oil and paraffin wax.

The wax and/or polishing composition can provide a means for incorporating and attaching perfumes, pest control ingredients, antimicrobials, including fungicides, and a host of other beneficial ingredients, especially those that are soluble, or dispersible, in the additive.

E. Additional Optional Components

The beneficial compositions of the present invention may contain optional components. Typical optional components in beneficial compositions intended for use on animate objects (skin, hair, or teeth) include, but are not limited to, hair colorants, odor absorbers, anti-irritants, drug and active delivery ingredients, water, pH reducing or buffering systems, vitamins, skin soothing agents, anti-inflammatories, viscosity modifiers, perfumes, disinfectant antibacterial actives, pharmaceutical actives, film formers, deodorants, opacifiers, astringents, waxes, anti-bacterials, anti-fungals, anti-virals, anti-oxidants, chelating agents, humectant/moisturizing agents, anti-rash agents, anti-redness agents, anti-itch agents, anti-histamines, solvents, naturals, botanicals, nutrients, surfactants, colorants, fragrances, zinc chloride, carbon, zinc oxide, enzyme inhibitors, fecal enzyme inhibitors, barrier protectants, anti-acne actives, anti-wrinkle actives, anti-microbial actives, anti-fungal actives, anti-inflammatory actives, topical anesthetic actives, artificial tanning agents and accelerators, anti-viral agents, enzymes, sunscreen actives, anti-oxidants, skin exfoliating agents, and combinations thereof.

For further guidance, additional examples of each of these types of optional ingredients, along with a listing of product categories in which they might be used (such as aftershaves, eye makeup removers, hair bleaches, skin fresheners, etc.) can be found in The International Cosmetic Ingredients Dictionary and Handbook, 8$^{th}$ Edition, 1999, which is incorporated herein by reference in its entirety.

IV. Achieving Desired Top-Bias of the Present Invention

The desired Top-Bias of the beneficial component on the treated substrates of present invention can be achieved via a number of approaches. One approach requires that the beneficial component comprise at least two separate layers. The first layer is either relatively hydrophilic or relatively hydrophobic to the second layer of the beneficial component. In yet another embodiment, both the first and second layers are part of the beneficial component, but their relative hydrophilicities and relative hydrophobicities are not critical. In another embodiment, the first support layer is not part of the beneficial component, but merely serves to support the beneficial component on the substrate prior to volatilizing away.

A. Relatively Hydrophilic Layers and Relatively Hydrophobic Layers

While not intended to be bound by theory, it is believed that this embodiment advantageously utilizes the relative hydrophilicities and hydrophobicities to aid in achieving the desired Top-Bias via a repulsive mechanism. Additional mechanisms may also be involved as mentioned below. In one embodiment, the first layer of beneficial component is relatively hydrophilic to the second layer of beneficial component (conversely, the second layer is relatively hydrophobic to the first layer). In a second embodiment, the first layer of beneficial component is relatively hydrophobic to the second layer of beneficial component (conversely, the second layer is relatively hydrophilic to the first layer). As used herein in describing layers of beneficial components, the term "layer" refers to a single component of the beneficial component. These layers may or may not be miscible to some degree. As used herein to describe the layer embodiments of this section, the term "first layer" means that this layer of beneficial component is disposed on at least a portion of the contacting surface of the substrate. As used herein to describe the layer embodiments of this section, the term "second layer" means that this layer of beneficial component is disposed on at least a portion of the first layer. The second layer may also be in contact with the contacting surface of the substrate. As used herein, the term "relatively hydrophilic" refers to a layer of the beneficial component which has a solubility parameter with a magnitude of >2 (calories/cubic centimeter)$^{1/2}$ more than the adjacent, relevant beneficial component layer's solubility parameter. For instance, if a first layer has a solubility parameter of 23 and the second layer has a solubility parameter of 8, then the first layer is relatively hydrophilic to the second layer. Similarly, as used herein, the term "relatively hydrophobic" refers to a layer of the beneficial component which has a solubility parameter with a magnitude of >2 (calories/cubic centimeter)$^{1/2}$ less than the adjacent beneficial component layer's solubility parameter. For instance, if a first layer has a solubility parameter of 8 and the second layer has a solubility parameter of 23, then the first layer is relatively hydrophobic to the second layer. It is to be understood that in discussing the first and second layers, the use of the phrases "relatively hydrophilic layer" and "relatively hydrophobic layer" mean relative to each other, not to an optional third layer. Where relativity to a third or other layer is intended, it will be explicitly stated.

The relatively hydrophilic layer typically comprises at least about 5% to at least about 95%, preferably 10% to at least about 90%, more preferably 20% to at least about 80%, of the beneficial component. The relatively hydrophilic layer is preferably added as a cold, polar composition particularly when it is the first layer. The relatively hydrophobic layer, typically comprises at least about 5% to at least about 95%, more preferably 10% to at least about 90%, still more preferably 20% to at least about 80%, of the beneficial component. The relatively hydrophobic layer is preferably added as a hot, non-polar composition which may be lipophobic particularly when it is the second layer.

The following lists provide non-limiting examples of layers which are relatively hydrophobic and relatively hydrophilic to each other. Components used alone or in combination with other components listed therein as "Layer A Components" are all relatively hydrophilic to "Layer B Components". Similarly, components used alone or in combination with other components listed therein as "Layer B Components" are all relatively hydrophobic to "Layer A Components".

Layer A Components (Relatively Hydrophilic to Layer B Components):

water, glycerin and polyglycerins, glycols such as polyethylene glycols and propylene glycol, polypropylene glycols, 2-methyl propanediol, glymes, ethers such as tripropylene glycol methyl ether, sugars such as glucose, ethoxylated alcohol surfactants such as steareth-100, ethylene glycol, polyethylene glycols, fatty alcohols, butylene glycol, urea, methanol, alcohols such as ethanol, inorganic salts such as sodium chloride, potassium chloride, and mixtures thereof.

Layer B Components (Relatively Hydrophobic to Layer A Components):

petrolatum, stearyl alcohol, mineral oil, lanolin and lanolin derivatives, squalane and squalene, vegetable oils such as olive oil and avocado oil, polydecene, glycerides and glyceride derivatives (e.g., triglycerides), essential fatty acids, butters such as cocoa and shea, emollient esters such as diisostearyl malate, isoparaffins, polyisobutylenes, silicones and silicone derivatives such as silicone waxes, waxes such as paraffin and microcrystalling waxes, natural waxes (e.g., bees wax) polyethylene, and mixtures thereof.

Thus, in the embodiment where the first layer is relatively hydrophilic to the second layer, the first layer could comprise one or more of the Layer A Components when the second layer comprises one or more of the Layer B Components. On the other hand, in the embodiment where the first layer is relatively hydrophobic to the second layer, the first layer could comprise one or more of the Layer B Components when the second layer comprises one or more of the Layer A Components.

Example A

Relatively Hydrophilic First Layer and Relatively Hydrophobic Second Layer

|  | Component | Solubility Parameter |
|---|---|---|
| First Layer | 40% polyethylene glycol 8000 | 15 |
|  | 60% Water | 23 |
| Second Layer | 20% Stearyl Alcohol | 9 |
|  | 80% Petrolatum | 7 |

Example B

Relatively Hydrophobic First Layer and Relatively Hydrophilic Second Layer

|  | Component | Solubility Parameter |
|---|---|---|
| First Layer | 20% Paraffin Wax | 7 |
|  | 80% Mineral Oil | 7 |
| Second Layer | 50% Glycerin | 16 |
|  | 50% Methyl Propanediol | 9 |

It is often preferable, particularly when the first layer is relatively hydrophilic, to include ingredients such as viscosity increasing agents into the relatively hydrophilic layer. Viscosity increasing agents help resist flow of the hydrophilic layer into the substrate. Viscosity increasing agents useful for this purpose include but are not limited to cellulose and cellulose derivatives such as cellulose gum and hydroxyethylcellulose, flours such as oat flour, magnesium silicate, polyacrylic acid, gums such as xantham gum, hectorite, guar and guar derivatives such as carboxymethyl hydroxypropyl guar, agar, bentonite carbomer, starches such as corn starch, gelatin, polyethylene glycols, and others listed in CTFA/$2^{ND}$ edition, published 1992.

It is often preferable, particularly when the first layer is relatively hydrophobic, to include ingredients which aid in keeping the hydrophobic layer at or near the uppermost region of the contacting surface of the substrate. Such ingredients include those which act as crystallization sites for the hydrophobic layer to solidify faster on the top surface of the substrate. These crystallization sites are typically straight chain in structure and include such materials as paraffin waxes and polyethylene waxes, or endothermic salts which absorb heat when wetted out. For example, endothermic materials such as potassium chloride and mannitol could be suspended in the hydrophobic matrix. Upon application of the hydrophilic layer, the endothermic heat absorbing reaction would be initiated to allow cooling and speed up solidification of both layers.

Additional/Optional Layers:

It is important to note that any of the embodiments and/or approaches described herein may additionally comprise other layers within the beneficial component. These additional layers may be added regardless of their relative hydrophilicities and hydrophobicities or may also be relatively hydrophobic or relatively hydrophilic to their adjacent layer(s). Typical additional layers may include perfumes and/or pure or highly concentrated optional ingredients. The use of such additional layers enables formulators to maximize the transfer of expensive optional ingredients to the intended surface as little or no portion of the layer will be sacrificed into the substrate.

General examples of such embodiments include beneficial components comprising a first relatively hydrophilic layer, a second relatively hydrophobic layer, and:

1. a third layer which is relatively hydrophilic to the second layer;
2. a third layer which is relatively hydrophobic to the second layer;
3. a third layer which is relatively hydrophilic to the second layer and a fourth layer which is relatively hydrophobic to the third layer;
4. a third layer which is relatively hydrophobic to the second layer and a fourth layer which is relatively hydrophilic to the third layer;
5. a third layer which is an emulsion or a microemulsion not meeting the requirements for being relatively hydrophilic nor relatively hydrophobic to the second layer; or
6. a third layer which is a single aqueous phase, not meeting the requirements for being relatively hydrophilic to the second layer and a fourth layer which is relatively hydrophobic to the third layer.

Alternately, the above exemplary additional layers can be included where the beneficial component comprises a first relatively hydrophobic layer and a second relatively hydrophilic layer. Other embodiments and/or variations can readily be envisioned by one of ordinary skill in the art given these examples. It is also understood that some of the additional/optional layers may mix with and/or form emulsions with other layers upon application.

B. Support Layer

While not intended to be limited in theory, it is believed that each of the "layer approaches" discussed above and following utilize, to some degree, occlusion of otherwise pervious regions of the substrate to aid in achieving the desired Top-Bias of a beneficial component on a substrate. Occlusion may be done by sacrificing some or all of a component in a first support layer in order to Top-Bias the second layer of the beneficial component. When this approach is taken, the relative hydrophilicities and hydrophobicities are irrelevant. For example, this can be accomplished by first applying a base lotion layer without the active component and then subsequently applying a lotion layer consisting of the same base lotion with an additional active component. This results in active placement adjacent to the wearer while minimizing active loss into the topsheet. Consequently, with the same quantity of lotion applied, less active would be required to deliver the same benefit.

C. Volatile Intermediaries

An alternate layering approach can be accomplished by first applying a volatile base layer to the substrate and then subsequently applying a second lotion layer comprising a lotion with an additional active component. The volatile first layer would then impede the migration of the second layer into the substrate and subsequently dissipate leaving only the second lotion layer. This results in active placement adjacent to the wearer while minimizing active loss into the topsheet. Examples of volatile base lotion layers include, but are not limited to, short chain alcohols (e.g., methanol, ethanol, isopropyl alcohol), short chain hydrocarbons and blends (e.g., hexane, dodecane, Permethyl®, Permethyl® 101a), and water.

V. General Process

One process for making the treated substrates using the structured layered approach described herein is set forth below. The first layer is dispensed on the contacting surface of the substrate followed by a second layer without the formation of an emulsion (i.e. some degree of phase separation between the layers is retained and the first layer does not completely dissolve or envelop the second layer), which generally rapidly solidifies as it is applied to the first layer which may solidify.

Any of a variety of application methods can be used to apply the beneficial component to the substrate. Suitable application methods include coating (e.g., gravure or slot coating), spraying, printing (e.g., flexographic printing), extruding, or combinations of these or other application techniques (e.g., spraying the beneficial component on a rotating surface, such as a calendar roll, that then transfers via contact coating the beneficial component to the body surface of the substrate). It is also possible to apply the first layer by dipping the substrate into the first layer or pouring/saturating the substrate with the first layer. This approach should not be used where the first layer is expensive as much of the first layer is sacrificed into the substrate.

The beneficial component may be applied evenly and uniformly onto the contacting surface of the substrate or portions thereof. If both surfaces of the substrate are intended to be contacting surfaces, the beneficial component may be applied to both surfaces. The beneficial component may also be applied in patterns or in random regions nonuniformly. By "nonuniform", it is meant that the amount, pattern of distribution, etc., of the beneficial component can vary over the substrate surface. For example, some portions of the treated surface of the substrate can have greater or lesser amounts of beneficial component, including portions of the surface that do not have any beneficial component on it. As applied to a substrate to be used as a topsheet of an absorbent article, the surface will have regions where no beneficial component is applied so as to allow for adequate liquid transfer through the untreated regions. Where the beneficial component is applied nonuniformly, any beneficial component pattern may be utilized, including, for example, application of small droplets (obtained via, e.g., spraying) discrete dots (obtained via, e.g., gravure printing), stripes that run in the longitudinal or lateral direction of the article, spirals, boxes, waves, figures, words, etc.

Some or all of the beneficial component can be applied to the substrate at any point during assembly. For example, the beneficial component can be applied to the substrate of the finished product before it has been packaged or the substrate could be supplied having all or a portion of the beneficial component on it (e.g., it could come as a pretreated substrate, already having the first layer of the beneficial component on the substrate). Some or all of the beneficial component can also be applied to the substrate before it is combined with the other raw materials to form a finished product.

VI. Top-Bias Determination

To determine Top-Bias, the beneficial component treated substrate is divided into thirds in the Z-direction. The thirds are then peeled apart and standard Gas Chromatography is subsequently used to determine the beneficial component content of each layer. The Top-Bias ratio is then determined by calculating the ratio of the beneficial component contained on or within the top third layer, between 0 and $Z/3$ (i.e., containing the contacting surface), to the bottom third layer, between $2Z/3$ and $Z$ (i.e., containing the opposing surface). Wherein the substrate is porous and liquid permeable, yet cannot be easily peeled apart into thirds for purposes of determining infringement, the beneficial component should be applied to a three layer laminate of 8.5 gsm nylon using the same method and amount as done on the treated substrate in question.

VII. EXAMPLES

A. Hydrophilic Layer

The following examples are intended to demonstrate the preparation of various skin care compositions.

| Example I | |
|---|---|
| Glycerin | 50% |
| Water | 50% |
| Total | 100% |
| Example II | |
| Oat Extract | 1% |
| Polyethylene Glycol 8000 | 40% |
| Water | 59% |
| Total | 100% |
| Example III | |
| Hydroxyethylcellulose | 2% |
| Zinc Oxide | 5% |
| Glycerin | 93% |
| Total | 100% |
| Example IV | |
| Hydroxyethylcellulose | 2% |
| Zinc Oxide | 5% |
| Polyethylene Glycol 8000 | 23% |
| Glycerin | 70% |
| Total | 100% |

B. Hydrophobic Layer

The following examples are intended to demonstrate the preparation of various skin care compositions.

| Example I | |
|---|---|
| Petrolatum | 59% |
| Stearyl Alcohol | 41% |
| Total | 100% |
| Alternately Add Aloe Solution | 1% |
| Example II | |
| Petrolatum, USP | 53% |
| Stearyl Alcohol, NF | 33% |
| Zinc Oxide Dispersion (74.4% ZnO) | 10% |
| Fumed Silica | 4% |
| Total | 100% |
| Example III | |
| Hexamidine Diisethionate | 1% |
| Beheneth-10 | 6% |

-continued

| | |
|---|---|
| Petrolatum | 73% |
| Behenyl Alcohol | 17% |
| Fumed Silica | 3% |
| Total | 100% |

C. Example of Top-Bias Calculation

Method of Making:

A Top-Biased lotion on a substrate is prepared on an unwind/rewind stand. The applicators are staged in the following order such that the web unwinds then contacts a glycerin/water sprayer, then a Uniform Fiber Deposition head (UFD, Sold by ITW/Dynatec) for lotion, then a water sprayer, and finally the rewind. The web moves at an approximate speed of 960 feet/minute. The UFD head applies an intermittent lotion pattern, with a frequency that is 70% on and 30% off. The glycerin/water sprayer and the water sprayer supply their respective solutions continuously, and at a pattern width of approximately 20 cm. The Lotion temperature is 70° C. and the glycerin/water and water temperatures are 20° C.

The lotion is applied at 0.48 g/m$^2$ via UFD in a 24 stripe pattern (1 mm width stripes) to a laminate constructed of three layers of 8.5 gsm nylon manufactured and adhered to a polymer backsheet.

Three conditions are completed as follows:
i. The first run is defined as the baseline condition, in which only lotion is applied to the substrate at 0.48 g/meter.
ii. In the second run, a mix of glycerin/water applied at a flow rate 0.65 g/meter is used to saturate the laminate before the lotion is added.
iii. As an optional final run, the glycerin/water is applied first, then the lotion, and then water is applied at a flow rate of 0.35 g/meter, as the final step.

Results:

Measurement of the location of the lotion in each condition and were taken according to the methodology set forth in section VI and results were as follows:

| Condition | Procedure | Top-Bias Ratio (1$^{st}$:3$^{rd}$ layer) |
|---|---|---|
| i | 1. Control | 2.1:1 |
| ii | 1. Glycerine/Water<br>2. Lotion | 2.9:1 |
| iii<br>(Optional) | 1. Glycerine Water<br>2. Lotion<br>3. Water | 3.7:1 |

The comparative example demonstrates an increase in Top-Bias from 2.1:1 in the control condition (i) to 2.9:1 in the condition using a means for minimizing migration of the beneficial component into the porous substrate of the present invention (ii). The optional condition (iii) also demonstrated an increase from control, 2.2:1 versus 3.7:1 respectively and represents another embodiment of the present invention in which an optional third layer, water, is added as part of the process.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. A method for Top-Biasing a composition on a porous substrate, the method comprising the following steps:
   a. applying a first layer of a relatively hydrophilic component on the porous substrate, wherein the relatively hydrophilic component comprises polyethylene glycol;
   b. applying a second layer of a relatively hydrophobic component on the relatively hydrophilic component; and
   c. allowing the first layer and second layer to simultaneously cool on the substrate without the formation of an emulsion.

2. The method of claim 1, wherein the relatively hydrophilic component further comprises glycerin, diols, urea, sodium chloride, water, and mixtures thereof.

3. The method of claim 1, wherein the relatively hydrophobic component is selected from the group consisting of petrolatum, stearyl alcohol, behenyl alcohol, mineral oil, silicone, lanolin, and mixtures thereof.

4. The method of claim 1, wherein the hydrophilic component further comprises a volatile intermediary.

5. The method of claim 1, wherein the first and second layers are incompatible/immiscible.

6. The method of claim 1, wherein the first and second layers make up a portion of a diaper.

7. The method of claim 1, wherein the first and second layers make up a portion of a feminine napkin.

8. The method of claim 1, wherein the first and second layers make up a portion of a pantiliner.

9. The method of claim 1, wherein the first and second layers make up a portion of an incontinence garment.

10. The method of claim 1, further comprising the step of applying a third layer of a component.

11. The method of claim 10, wherein the third layer disposed on at least a portion of the second layer.

12. The method of claim 10, wherein the third layer comprises a relatively hydrophilic component.

13. The method of claim 12, wherein the third layer comprises polyethylene glycol.

14. The method of claim 10, further comprising the step of allowing the first, second, and third layers to simultaneously cool on the substrate without the formation of an emulsion.

15. The method of claim 12, wherein the third layer comprises a volatile intermediary.

16. The method of claim 10, wherein the third layer comprises glycerin, diols, urea, sodium chloride, water, and mixtures thereof.

* * * * *